United States Patent [19]

Taylor et al.

[11] 4,044,142
[45] Aug. 23, 1977

[54] 1,2-DIHYDRO-6-PHENYL-1H,4H-IMIDAZOBENZODIAZEPIN-1-ONES

[75] Inventors: John Bodenham Taylor, Down Ampney, near Cirencester; Derek Ralph Harrison, Swindon, both of England

[73] Assignee: Roussel Uclaf, Paris, France

[21] Appl. No.: 658,301

[22] Filed: Feb. 17, 1976

[30] Foreign Application Priority Data

Feb. 15, 1975 United Kingdom ............... 6509/75
Nov. 4, 1975 United Kingdom ............... 4580/75

[51] Int. Cl.² .......................................... C07D 403/14
[52] U.S. Cl. ......................... 424/250; 542/412; 542/436; 542/444; 260/326.8; 260/293.51; 260/268 PC; 424/267; 260/243.3; 548/302
[58] Field of Search ............ 260/240.3, 309.6, 268 PC; 424/250

[56] References Cited

U.S. PATENT DOCUMENTS 3,846,443 11/1974 Moffett .............................. 260/309.7
3,920,687 11/1975 Buzby et al. ....................... 260/309.6

FOREIGN PATENT DOCUMENTS 2,183,716 12/1973 France

*Primary Examiner*—Arthur P. Demers
*Attorney, Agent, or Firm*—Hammond & Littell

[57] ABSTRACT

Novel 1,2-dihydro-6-phenyl-1H,4H-imidazo[1,2-a][1,4]-benzodiazepin-1-ones of the formula

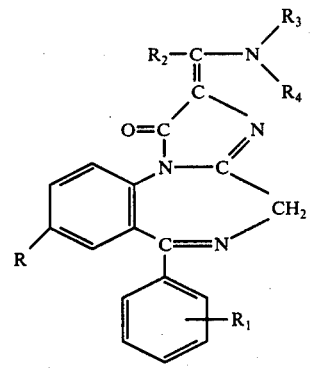

wherein R is selected from the group consisting of hydrogen, halogen, nitro and trifluoromethyl, $R_1$ is selected from the group consisting of hydrogen and halogen, $R_2$ is selected from the group consisting of hydrogen and methyl and $R_3$ and $R_4$ are individually selected from the group consisting of hydrogen, alkyl of 1 to 5 carbon atoms, hydroxyalkyl of 1 to 5 carbon atoms, aminoalkyl of 1 to 5 carbon atoms, mono- and di-alkylaminoalkyl with each alkyl having 1 to 5 carbon atoms, cycloalkyl of 3 to 8 carbon atoms and mono and di-nuclear aryl or $R_3$ and $R_4$ taken together with the nitrogen atom to which they are attached form a saturated heterocycle which may contain a second heteroatom optionally substituted with at least one member of the group consisting of alkyl of 1 to 5 carbon atoms, hydroxyalkyl of 1 to 5 carbon atoms, dialkylphosphinylalkyl with 1 to 5 carbon atoms in the alkyl groups, cycloalkylalkyl with 3 to 6 carbon atoms in the ring and 1 to 5 alkyl carbon atoms, alkenyl of 2 to 5 carbon atoms, phenyl and nitrogen heterocycles and their nontoxic, pharmaceutically acceptable acid addition salts having sedative, hypnotic, anxiolytic, tranquilizing, anticonvulsive and myorelaxant properties and their preparation.

21 Claims, No Drawings

1,2-DIHYDRO-6-PHENYL-1H,4H-IMIDAZOBENZODIAZEPIN-1-ONES

STATE OF THE ART

French Pat. No. 2,183,716 describes benzodiazepines but they are differently substituted than the compounds of formula I and have tranquilizing properties.

OBJECTS OF THE INVENTION

It is an object of the invention to provide the novel compounds of formula I and their non-toxic, pharmaceutically acceptable acid addition salts and their preparation.

It is another object of the invention to provide novel therapeutic compositions and a novel method of treating agitated states, insomnia and psychosomatic syndromes in warm-blooded animals.

These and other objects and advantages of the invention will become obvious from the following detailed description.

THE INVENTION

The novel compounds of the invention are 1,2-dihydro-6-phenyl-1H,4H-imidazo-[1,2-a][1,4]-benzodiazepin-1-ones of the formula

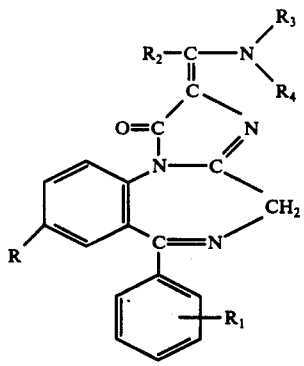

I

Wherein R is selected from the group consisting of hydrogen, halogen, nitro and trifluoromethyl, $R_1$ is selected from the group consisting of hydrogen and halogen, $R_2$ is selected from the group consisting of hydrogen and methyl and $R_3$ and $R_4$ are individually selected from the group consisting of hydrogen, alkyl of 1 to 5 carbon atoms, hydroxyalkyl of 1 to 5 carbon atoms, aminoalkyl of 1 to 5 carbon atoms, mono- and dialkylaminoalkyl with each alkyl having 1 to 5 carbon atoms, cycloalkyl of 3 to 8 carbon atoms and mono and di-nuclear aryl or $R_3$ and $R_4$ taken together with the nitrogen atom to which they are attached form a saturated heterocycle which may contain a second heteroatom optionally substituted with at least one member of the group consisting of alkyl of 1 to 5 carbon atoms, hydroxyalkyl of 1 to 5 carbon atoms, dialkylphosphinylalkyl with 1 to 5 carbon atoms in the alkyl groups, cycloalkylalkyl with 3 to 6 carbon atoms in the ring and 1 to 5 alkyl carbon atoms, alkenyl of 2 to 5 carbon atoms, phenyl and nitrogen heterocycles and their non-toxic, pharmaceutically acceptable acid addition salts.

When R and $R_1$ are halogen, they may be fluorine, chlorine or bromine and R is preferably chlorine and $R_1$ is preferably fluorine or chlorine in the ortho position although it may be in other positions. $R_2$ is preferably hydrogen.

$R_3$ and $R_4$ may be alkyl such as methyl, ethyl, propyl, isopropyl, butyl, isobutyl, tert.-butyl or pentyl but is preferably a linear alkyl of 1 to 4 carbon atoms. Examples of hydroxyalkyl are hydroxymethyl, hydroxyethyl, hydroxypropyl, hydroxybutyl or hydroxypentyl but is preferably hydroxyethyl. Examples of aminoalkyl and mono- and dialkylaminoalkyl groups are those where the alkyl may be methyl, ethyl, propyl, butyl but preferably are methyl or ethyl. Specific groups are preferably aminomethyl, aminoethyl, dimethylaminoethyl and diethylaminoethyl but may also be aminopropyl, aminobutyl, methylaminomethyl, methylaminoethyl and dimethylaminopropyl. When $R_3$ or $R_4$ are aryl, they may be phenyl or naphthyl, preferably phenyl. An example of cycloalkyl of 3 to 8 carbon atoms is cyclohexyl. When $R_3$ and $R_4$ are different, one of them is preferably hydrogen.

When $R_3$ and $R_4$, together with the nitrogen atom to which they are attached form a heterocyclic, it is saturated and may be substituted or unsubstituted and may optionally contain a second heteroatom. Examples of unsubstituted heterocyclics are pyrrolidinyl, piperidino, morpholino, thiomorpholino and piperazin-1-yl. Preferred substituents for such heterocyclic groupings are alkyls of 1 to 5 carbon atoms such as methyl, ethyl and propyl; hydroxyalkyls of 1 to 5 carbon atoms such as hydroxyethyl; dialkylphosphinylalkyls, each alkyl moiety of which contains from 1 to 5 carbon atoms such as methyl; cycloalkylalkyls with 3 to 6 carbon atoms in the cycloalkyl moiety and 1 to 5 alkyl carbon atoms such as cyclopropylmethyl; alkenyls of 2 to 5 carbon atoms such as allyl; phenyl; and nitrogen heterocyclic radicals such as 1-phenyl-5-imidazolyl-4-one.

Typical examples of substituted heterocyclics are the 4-alkyl-piperazin-1-yls and especially 4-methyl-, 4-ethyl- and 4-propyl-piperazin-1-yl; the 4-hydroxyalkyl-piperazin-1-yls and especially 4-hydroxyethyl-piperazin-1-yl; the 4-dialkylphosphinylalkyl-piperazin-1-yls and especially 4-dimethylphosphinylmethyl-piperazin-1-yl; the 4-cycloalkylalkyl-piperazin-1-yls and especially 4-cyclopropylmethyl-piperazin-1-yl; 4-alkenyl-piperazin-1-yls and especially 4-allyl-piperazin-1-yl; 4-phenyl-piperazin-1-yl; and 4-(1'-phenyl-5'-imidazoyl-4'-one)-piperidin-1-yl.

A preferred group of compounds are the imidazolobenzodiazepines of formula I wherein $R_3$ and $R_4$ are individually selected from the group consisting of hydrogen, alkyl of 1 to 5 carbon atoms, hydroxyethyl, dimethyl- or diethylaminoethyl, phenyl and cyclohexyl or $R_3$ and $R_4$ together with the nitrogen atom form a member of the group consisting of pyrrolidinyl, piperidino, morpholino, thiomorpholino, piperazin-1-yl, 4-alkyl-piperazin-1-yl, 4-hydroxyalkyl-piperazin-1-yl, 4-phenyl-piperazin-1-yl and 4-(1'-phenyl-5'-imidazolyl-4'-one)piperidin-1-yl.

A second preferred group of compounds are the imidazolobenzodiazepines of formula I wherein R is chlorine or nitro, $R_1$ is selected from the group consisting of hydrogen, chlorine and fluorine, $R_2$ is hydrogen, and $R_3$ and $R_4$ are individually selected from the group consisting of hydrogen, straight alkyl of 1 to 5 carbon atoms, hydroxyethyl, phenyl and cyclohexyl, or $R_3$ and $R_4$ together with the nitrogen atom form a member selected from the group consisting of piperidino, morpholino, piperazin-1-yl, 4-alkyl-piperazin-1-yl and 4-hydroxyethyl-piperazin-1-yl.

A third preferred group of compounds are the imidazolobenzodiazepines of formula I wherein R is chlorine or nitro, $R_1$ is hydrogen, chlorine or fluorine, $R_2$ is hydrogen, and $R_3$ is hydrogen and $R_4$ is methyl, ethyl, propyl or butyl, or $R_3$ and $R_4$ together with the nitrogen atom form a member selected from the group consisting of piperazin-1-yl, 4-methyl-piperazin-1-yl, 4-ethyl-piperazin-1-yl, 4-propyl-piperazin-1-yl and 4-hydroxyethyl-piperazin-1-yl.

A fourth group of preferred compounds are the imidazolobenzodiazepines of formula I wherein R is chlorine or nitro, $R_1$ is hydrogen, chlorine or fluorine, $R_2$ is hydrogen, and $R_3$ and $R_4$ together with the nitrogen atom form a 4-methyl-piperazin-1-yl, 4-ethyl-piperazin-1-yl or 4-propyl-piperazin-1-yl radical.

A fifth group of preferred compounds are the imidazolobenzodiazepines of formula I wherein R is hydrogen, chlorine or nitro, $R_1$ is hydrogen, chlorine or fluorine, $R_2$ is hydrogen and $R_3$ and $R_4$ together with the nitrogen atom form a 4-dialkylphosphinylalkyl-piperazin-1-yl radical; and the imidazolobenzodiazepines of formula I wherein R is hydrogen, chlorine or nitro, $R_1$ is hydrogen or chlorine, $R_2$ is hydrogen and $R_3$ and $R_4$ together with the nitrogen atom form a 4-dimethylphosphinylmethyl-piperazin-1-yl radical.

The imidazolobenzodiazepines I may be in the form of non-toxic, pharmaceutically acceptable acid addition salts which may be salts with mineral or organic acids. Typical mineral acids are hydrochloric acid, hydrobromic acid, hydroiodic acid, nitric acid, sulfuric acid and phosphoric acid, while typical organic acids are acetic acid, formic acid, benzoic acid, maleic acid, fumaric acid, succinic acid, tartaric acid, citric acid, oxalic acid, glyoxylic acid, aspartic acid, alkanesulfonic acids and arylsulfonic acids. Preferred acid addition salts are the tartrates and alkanesulfonates, and the methanesulfonates are especially preferred.

Further preferred groups of compounds of the invention in the form of acid addition salts are the acid addition salts of imidazolobenzodiazepines of formula I wherein R is hydrogen, chlorine or nitro, $R_1$ is hydrogen, chlorine or fluorine, $R_2$ is hydrogen and $R_3$ and $R_4$ together with the nitrogen atom form a 4-alkyl-piperazin-1-yl radical; and the tartrates and alkanesulfonates (particularly methanesulfonates) of the imidazolobenzodiazepines of formula I wherein R is chlorine or nitro, $R_1$ is hydrogen or chlorine, $R_2$ is hydrogen and $R_3$ and $R_4$ together with the nitrogen atom form a 4-methyl-piperazin-1-yl or a 4-ethyl-piperazin-1-yl.

Specific preferred imidazolobenzodiazepines of formula I and their non-toxic, pharmaceutically acceptable salts are:

8-chloro-1,2-dihydro-2-(N-methyl-piperazin-1-yl) methylene-6-phenyl-1H,4H-imidazo-[1,2-a][1,4]-benzodiazepin-1-one;

8-chloro-1,2-dihydro-2-(N-methyl-piperazin-1-yl) methylene-6-phenyl-1H,4H-imidazo-[1,2-a][1,4]-benzodiazepin-1-one tartrate;

8-chloro-1,2-dihydro-2(N-hydroxyethyl-piperazin-1-yl) methylene-6-phenyl-1H,4H-imidazo-[1,2-a][1,4]-benzodiazepin-1-one;

8-chloro-1,2-dihydro-2-(N-methyl-piperazin-1-yl) methylene-6-(o-chlorophenyl)-1H,4H-imidazo-[1,2-a][1,4]-benzodiazepin-1-one;

8-chloro-1,2-dihydro-2-(N-methyl-piperazin-1-yl) methylene-6-(o-chlorophenyl)-1H,4H-imidazo-[1,2-a][1,4]-benzodiazepin-1-one tartrate;

8-nitro-1,2-dihydro-2-(N-methyl-piperazin-1-yl) methylene-6-phenyl-1H,4H-imidazo-[1,2-a][1,4]-benzodiazepin-1-one;

8-chloro-1,2-dihydro-2-(n-butyl-amino) methylene-6-phenyl-1H,4H-imidazo-[1,2-a][1,4]-benzodiazepin-1-one;

8-chloro-1,2-dihydro-2-(N-methyl-piperazin-1-yl) methylene-6-(o-fluorophenyl)-1H,4H-imidazol-[1,2-a][1,4]-benzodiazepin-1-one;

8-chloro-1,2-dihydro-2-(n-propylamino) methylene-6-phenyl-1H,4H-imidazo-[1,2-a][1,4]-benzodiazepin-1-one;

8-nitro-1,2-dihydro-2-(N-methyl-piperazin-1-yl) methylene-6-(o-chlorophenyl)-1H,4H-imidazo-[1,2-a][1,4]-benzodiazepin-1-one;

8-nitro-1,2-dihydro-2-(N-methyl-piperazin-1-yl) methylene-6-(o-chlorophenyl)-1H,4H-imidazo-[1,2-a][1,4]-benzodiazepin-1-one methanesulfonate;

8-nitro-1,2-dihydro-2-(N-methyl-piperazin-1-yl) methylene-6-(o-fluorophenyl)-1H,4H-imidazo-[1,2-a][1,4]-benzodiazepin-1-one;

8-chloro-1,2-dihydro-2-(N-ethyl-piperazin-1-yl) methylene-6-phenyl-1H,4H-imidazo-[1,2-a][1,4]-benzodiazepin-1-one;

8-chloro-1,2-dihydro-2-(N-propyl-piperazin-1-yl) methylene-6-phenyl-1H,4H-imidazo-[1,2-a][1,4]-benzodiazepin-1-one;

8-chloro-1,2-dihydro-2-(N-ethyl-piperazin-1-yl) methylene-6-(o-chlorophenyl)-1H,4H-imidazo-[1,2-a][1,4]-benzodiazepin-1-one;

8-chloro-1,2-dihydro-2-(N-ethyl-piperazin-1-yl) methylene-6(o-fluorophenyl)-1H,4H-imidazo-[1,2-a][1,4]-benzodiazepin-1-one;

8-nitro-1,2-dihydro-2-(N-ethyl-piperazin-1-yl) methylene-6-(o-chlorophenyl)-1H,4H-imidazo-[1,2-a][1,4]-benzodiazepin-1-one;

8-nitro-1,2-dihydro-2-(N-ethyl-piperazin-1-yl) methylene-6-(o-fluorophenyl)-1H,4H-imidazo-[1,2-a][1,4]-benzodiazepin-1-one;

8-chloro-1,2-dihydro-2-(ethylamino) methylene-6-phenyl-1H,4H-imidazo-[1,2-a][1,4]-benzodiazepin-1-one;

8-chloro-1,2-dihydro-2-(N-dimethylphosphinylmethyl-piperazin-1-yl) methylene-6-phenyl-1H,4H-imidazo-[1,2-a][1,4]-benzodiazepin-1-one;

8-chloro-1,2-dihydro-2-(N-dimethylphosphinylmethyl-piperazin-1-yl) methylene-6-(o-chlorophenyl)-1H,4H-imidazo-[1,2-a][1,4]-benzodiazepin-1-one;

1,2-dihydro-2-(N-dimethylphosphinylmethyl-piperazin-1-yl) methylene-6-phenyl-1H,4H-imidazo-[1,2-a][1,4]-benzodiazepin-1-one; and 8-nitro-1,2-dihydro-2-(N-dimethylphosphinylmethyl-piperazin-1-yl) methylene-6-(o-chlorophenyl)-1H,4H-imidazo-[1,2-a][1,4]-benzodiazepin-1-one. Of these specific preferred compounds, 8-nitro-1,2-dihydro-2-(N-methyl-piperazin-1-yl) methylene-6-(o-chlorophenyl)-1H,4H-imidazo-[1,2-a][1,4]-benzodiazepin-1-one methanesulfonate has shown a particularly remarkable pharmacological activity.

The imidazolobenzodiazepines of formula I may be prepared by reacting a compound of the formula

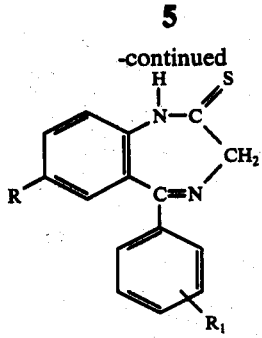

wherein R and $R_1$ have the above definition and glycine and alkyl esters thereof, preferably in an organic solvent such as an alcohol like ethanol at elevated temperatures such as the reflux temperature to obtain a compound of the formula

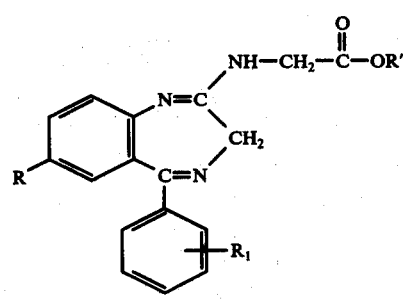

III wherein R' is hydrogen or alkyl and reacting the latter with a dehydrating agent such as carbodiimide like dicyclohexylcarbodiimide in a chlorinated alkane such as methylene chloride or subjecting the latter to pyrolysis in a high boiling solvent such as toluene to obtain the corresponding 8-R-1,2-dihydro-6-($R_1$-phenyl)-1H,4H-imidazo-[1,2-a][1,4]-benzodiazepin-1-one of the formula

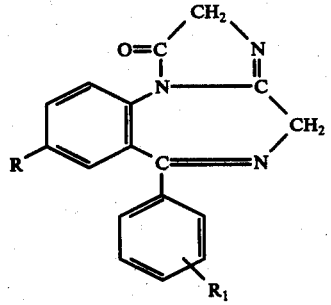

IV wherein R and $R_1$ have the above definition.

To obtain a compound of formula I wherein $R_2$ is hydrogen and $R_3$ and $R_4$ are methyl, the compound of formula IV may then be reacted with a dimethylformamide acetal of the formula

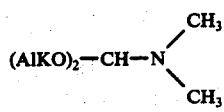

V wherein AlK is alkyl of 1 to 5 carbon atoms, preferably in an anhydrous organic solvent such as benzene in the presence of a base such as triethylamine or other nitrogen base or amine to form a compound of the formula

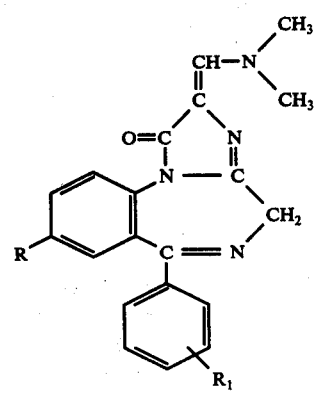

Ia wherein R and $R_1$ have the above definition.

To produce the compounds of formula I wherein $R_2$, $R_3$ and $R_4$ are all methyl, the compound of formula IV is reacted with N,N-dimethylacetamide preferably in an anhydrous organic solvent such as a chlorinated alkane like methylene chloride at a temperature below room temperature, i.e. below 10° C in the presence of a condensation promoter such as phosphorus oxychloride to obtain a compound of the formula

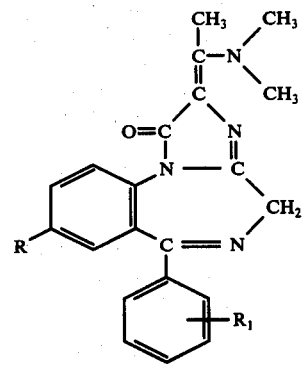

Ib wherein R and $R_1$ have the above definition.

To obtain the compounds of formula I wherein $R_3$ and $R_4$ are other than methyl, the compounds of formula Ia or Ib are transaminated with the appropriate amine or ammonia, preferably in an anhydrous organic solvent such as toluene at elevated temperatures such as reflux to obtain the corresponding compound of the formula Ic -continued

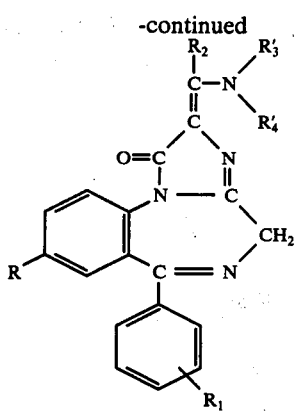

wherein R, R₁ and R₂ have the above definition and R'₃ and R'₄ are the same as R₃ and R₄ other than methyl.

The compounds of formula c may be further reacted, if necessary, to introduce the substituent on the heterocyclic ring. When

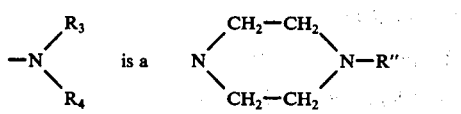

wherein R" is cycloalkylalkyl or alkenyl or dialkylphosphinylalkyl, the corresponding piperazinyl-1-yl compound is reacted with R"-Hal to form the corresponding R"-piperazin-1yl compound.

To produce the compounds of formula c wherein

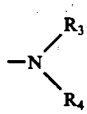

are 4-dialkylphosphinylalkyl-piperazin-1-yl, the compound of formula Ic is reacted with piperazine and the resulting compound is reacted with a haloalkyl dialkylphosphineoxide to obtain the corresponding 2-(n-dialkylphosphinylalkyl-piperazin-1-yl) compound. The latter reaction is preferably effected with the chloroalkyl-dialkylphosphine oxide in an organic solvent such as toluene.

The acid addition salts of the compounds of formula I may be formed by reaction with a substantially stoichiometric amount of the desired acid in an organic solvent such as alkanols such as methanol or ethanol or alkyl halides such as methylene chloride.

The 2-carboxymethylamino-7-R-5-(R₁-phenyl)-3H-1,4benzodiazepines of formula III and the corresponding 2-alkoxycarbonylmethylamino-7-R-5-(R₁-phenyl)-3H-1,4-benzodiazepines wherein the alkoxy group is other than ethoxy of formula III are novel products.

The novel pharmaceutical compositions of the invention are comprised of an effective amount of at least one compound of formula I and its non-toxic, pharmaceutically acceptable acid addition salts and a pharmaceutical carrier. The compositions may be in the form of a tablet, coated tablets, sublingual tablet, capsules, cachets, suppositories, syrups, drinkable solutions or suspensions and injectable solutions or suspensions.

The compositions may contain the usual pharmaceutical excipients such as talc, gum arabic, lactose, starch, animal or vegetable fats and oils, magnesium stearate, cacao butter, aqueous or non-aqueous liquids, paraffinic derivatives, glycols, wetting agents, dispersing agents, emulsifiers and preservatives.

The pharmaceutical compositions of the invention have sedative, hypnotic, anxiolytic, tranquilizing, anticonvulsive an myorelaxant activities and are useful for the treatment of states of agitation and irritability, states of aggression, insomnia, certain psychosomatic syndromes, certain character and behavior disorders and muscular contractions or spasms.

The novel method of the invention for treating agitated states, insomnia and psychosomatic syndromes in warm-blooded animals, including humans, comprises administering to warm-blooded animals an effective amount of at least one compound of formula I and its non-toxic, pharmaceutically acceptable acid addition salts. The compounds may be administered orally, rectally or transcutaneously and the usual daily dose is 0.02 to 1 mg/kg depending upon the compound and the method of administration.

In the following examples there are described several preferred embodiments to illustrate the invention. However, it is to be understood that the invention is not intended to be limited to the specific embodiments.

EXAMPLE 1

8-chloro-1,2-dihydro-2-(dimethylamino)methylene-6-phenyl-1H,4H-imidazo-[1,2-a][1,4]-benzodiazepin-1-one

STEP A:

2-carboxymethylamino-7-chloro-5-phenyl-3H-1,4-benzodiazepine

A suspension of 3.5 g of 7-chloro-1,3-dihydro-5-phenyl-2H-1,4-benzodiazepine-2-thione, 5.5 g of glycine, 5.5 g of sodium carbonate, 100 ml of ethanol and 30 ml of water was refluxed with stirring for an hour and the mixture was poured into water. The pH of the solution was adjusted to 4 by addition of 2N hydrochloric acid and was extracted with chloroform. The mixture was filtered and the filtrate was dried over magnesium sulfate and evaporated to dryness. The gummy residue was crystallized by trituration with methanol and the mixture was filtered. The recovered solid was crystallized from ethanol to obtain 3.1 g (77% yield) of 2-carboxymethylamino-7-chloro-5-phenyl-3H-1,4-benzodiazepine melting at 215°–220° C.

STEP B:

8-chloro-1,2-dihydro-6-phenyl-1H,4H-imidazo-[1,2-a][1,4]-benzodiazepin-1-one 2.1 g of dicyclohexylcarbodiimide were added with stirring to a suspension of 2.5 g of 2-carboxymethylamino-7-chloro-5-phenyl-3H-1,4-benzodiazepine in 120 ml of anhydrous methylene chloride and the mixture was stirred at room temperature for 3 hours and was filtered. The filtrate was evaporated to dryness to obtain 8-chloro-1,2-dihydro-6-phenyl-1H,4H-imidazo-[1,2-a][1,4]-benzodiazepin-1-one in the form of a colorless oil which was used as is for the next step.

STEP C: 8-chloro-1,2-dihydro-2-(dimethylamino)methylene-6-phenyl-1H,4H-imidazo-[1,2-a][1,4]-benzodiazepin-1-one 1.5 g of dimethylformamide diethyl acetal and 1 ml of triethylamine were added to a solution of the product of Step B in anhydrous benzene and the mixture was stirred at room temperature for 90 minutes. The mixture was evaporated to dryness and the brown-yellow residue was crystallized from ethyl acetate-methanol to obtain 2.7 g (97% yield) of 8-chloro-1,2-dihydro-2-(dimethylamino) methylene-6-phenyl-1H, 4H-imidazo-[1,2-a][1,4]-benzodiazepin-1-one in the form of pale yellow rods melting at 264°–265° C.

Analysis: $C_{20}H_{17}Cl\ N_4O$; molecular weight = 364.9

| | %C 65.85 | %H 4.66 | %N 15.37 | %Cl 9.74 |
|---|---|---|---|---|
| Calculated: | 65.85 | 4.66 | 15.37 | 9.74 |
| Found: | 65.87 | 4.67 | 15.37 | 9.79 |

I.R. Spectra (KBr disc):
C=O at 1690 cm$^{-1}$; C=N at 1621 cm$^{-1}$.

EXAMPLE 2

Using the procedure of Example 1, glycine was reacted with the appropriate benzodiazepine-2-thione to obtain a 66% yield of 2-carboxymethylamino-7-nitro-5-phenyl-3H-1,4-benzodiazepine which after crystallization melted at 154°–155° C. The said product was reacted with dicyclohexylcarbodiimide to form 8-nitro-1,2-dihydro-6-phenyl-1H,4H-imidazo-[1,2-a] [1,4]-benzodiazepin-1-one which was used as is for the reaction with dimethylformamide diethyl acetal to obtain after crystallization from methanol a 43% yield of 8-nitro-1,2-dihydro-2-(dimethylamino) methylene-6-phenyl-1H,4H-imidazo [1,2-a][1,4]-benzodiazepin-1-one melting at 227°–228° C.

EXAMPLE 3

Using the procedure of Example 1, glycine was reacted with the appropriate benzodiazepine-2-thione to obtain a 75% yield of 2-carboxymethylamino-7-chloro-5-o-chlorophenyl-3H-1,4-benzodiazepine which after crystallization from methanol-ethyl ether melted at 136°–139° C. The said product was reacted with dicyclohexylcarbodiimide to form 8-chloro-1,2-dihydro-6-o-chlorophenyl-1H,4H-imidazo-[1,2-a][1,4]-benzodiazepin-1-one which was used as is for the reaction with dimethylformamide diethyl acetal to obtain after crystallization from methanol-ethyl ether a 53% yield of 8-chloro-1,2-dihydro-2-(dimethylamino) methylene-6-o-chlorophenyl-1H, 4H-imidazo-[1,2-a][1,4]-benzodiazepin-1-one melting at 288°–290° C.

EXAMPLE 4

Using the procedure of Example 1, glycine was reacted with the appropriate benzodiazepine-2-thione to obtain a 83% yield of 2-carboxymethylamino-7-nitro-5-o-chlorophenyl-3H-1,4-benzodiazepine which after crystallization from ethyl ether melted at 158°–161° C. The said product was reacted with dicyclohexylcarbodiimide to form 8-nitro-1,2-dihydro-6-o-chlorophenyl-1H,4H-imidazo-[1,2-a][1,4]-benzodiazepin-1-one which was used as is for the reaction with dimethylformamide diethyl acetal to obtain after crystallization from methanol a 78% yield of 8-nitro-1,2-dihydro-2-(dimethylamino) methylene-6-o-chlorophenyl-1H,4H-imidazo-[1,2-a][1,4]-benzodiazepin-1-one melting at 253°–255° C.

EXAMPLE 5

Using the procedure of Example 1, glycine was reacted with the appropriate benzodiazepine-2-thione to obtain a 69% yield of 2-carboxymethylamino-7-chloro-5-o-fluorophenyl-3H-1,4-benzodiazepine in the form of a gum. The said product was reacted with dicyclohexylcarbodiimide to form 8-chloro-1,2-dihydro-6-o-fluorophenyl-1H,4H-imidazo-[1,2-a][1,4]-benzodiazepin-1-one which was used as is for the reaction with dimethylformamide diethyl acetal to obtain after crystallization from methanol a 63% yield of 8-chloro-1,2-dihydro-2-(dimethylamino) methylene-6-o-fluorophenyl-1H,4H-imidazo-[1,2-a][1,4]-benzodiazepin-1-one melting at 257°–260° C.

EXAMPLE 6

Using the procedure of Example 1, glycine was reacted with the appropriate benzodiazepine-2-thione to obtain a 44% yield of 2-carboxymethylamino-7-nitro-5-o-fluorophenyl-3H-1,4-benzodiazepine which was crystallized from ethyl ether. The said product was reacted with dicyclohexylcarbodiimide to form 8-nitro-1,2-dihydro-6-o-fluorophenyl-1H,4H-imidazo-[1,2-a][1,4]-benzodiazepin-1-one which was used as is for the reaction with dimethylformamide diethyl acetal to obtain after crystallization from methanol a 80% yield of 8-nitro-1,2-dihydro-2-(dimethylamino) methylene-6-o-fluorophenyl-1H,4H-imidazo-[1,2-a][1,4]-benzodiazepin-1-one melting at 228°–231° C.

EXAMPLE 7

8-chloro-2-[1'-(dimethylamino)ethylidene]-1,2-dihydro-6-phenyl-1H,4H-imidazo-[1,2-a][1,4]-benzodiazepin-1-one 3.7 g of phosphorus oxychloride were added dropwise over 5 minutes with stirring to a solution of 8-chloro-1,2-dihydro-6-phenyl-1H,4H-imidazo-[1,2-a][1,4]-benzodiazepin-1-one in 200 ml of methylene chloride and 2.0 g of dimethylacetamide cooled to 0° C and the mixture was stirred for 20 hours at room temperature and was poured into 500 ml of saturated sodium bicarbonate solution. The mixture was stirred until carbon dioxide evolution ceased and the aqueous layer was extracted twice with 100 ml of methylene chloride. The combined organic extracts were washed with saturated sodium bicarbonate solution and then water, were dried over magnesium sulfate and evaporated to dryness to obtain a yellow solid residue. The product was crystallized from a chloroformethyl ether mixture to obtain 2.3 g (40% yield) of 8-chloro-2-[1'-(dimethylamino)ethylidene]-1,2-dihydro-6-phenyl-1H,4H-imidazo-[1,2-a][1,4]-benzodiazepin-1-one melting at 251-252° C.

Analysis: $C_{21}H_{19}Cl\ N_4O$; molecular weight = 378.9

| | %C 66.58 | %H 5.02 | %N 14.79 | %Cl 9.38 |
|---|---|---|---|---|
| Calculated: | 66.58 | 5.02 | 14.79 | 9.38 |
| Found: | 66.32 | 4.91 | 14.77 | 9.02 |

I.R. Spectra (KBr disc):
C=O at 1653 cm$^{-1}$; C=N at 1610 cm$^{-1}$

EXAMPLE 8

8-chloro-1,2-dihydro-2-(N-methylpiperazin-1-yl) methylene-6-phenyl-1H,4H-imidazo-[1,2-a][1,4]-benzodiazepin-1-one and its tartrate

STEP A :

A mixture of 2.3 g of 8-chloro-1,2-dihydro-2-(dimethylamino) methylene-6-phenyl-1H,4H-imidazo-[1,2-a][1,4]-benzodiazepin-1-one and 4.0 g of N-methyl-piperazine in 50 ml of anhydrous toluene was refluxed for 24 hours and was cooled. The mixture was filtered and the filtrate was evaporated to dryness. The pale yellow residue was treated with methanol and the solution was filtered. The solid was crystallized from an ethyl acetate-methanol mixture to obtain 2.3 g (87% yield) of 8-chloro-1,2-dihydro-2-(N-methylpiperazin-1yl) methylene-6-phenyl-1H,4H-imidazo-[1,2-a][1,4]-benzodiazepin-1-one melting at 255°–256° C.

Analysis: $C_{23}H_{22}Cl\ N_5O$; molecular weight = 419.9

| | | | | |
|---|---|---|---|---|
| Calculated: | %C 65.80 | %H 5.24 | %N 16.69 | %Cl 8.46 |
| Found: | 65.64 | 5.27 | 16.63 | 8.56 |

I.R. Spectra (KBr disc):
C=O at 1705 cm$^{-1}$; C=N at 1635 cm$^{-1}$

STEP B:

A stoichiometric amount of the said product and tartaric acid in methanol was prepared and the mixture was filtered. The product was crystallized from methanol to obtain the tartrate of the said product melting at 146°–150° C.

Analysis: $C_{27}H_{28}Cl\ N_5O_7$; molecular weight = 570.1

| | | | | |
|---|---|---|---|---|
| Calculated: | %C 56.89 | %H 4.92 | %N 11.29 | %Cl 6.23 |
| Found: | 56.44 | 4.93 | 11.79 | 5.93 |

I.R. Spectra (KBr disc):
OH at 3400 cm$^{-1}$ and 2500 cm$^{-1}$; C=O at 1730 cm$^{-1}$ and 1690 cm$^{-1}$, C=N at 1630 cm$^{-1}$.

EXAMPLES 9 to 40

Using the procedure of Example 8, the 1,2-dihydro-2-(dimethylamino) methylene-6-phenyl-1H,4H-imidazo[1,2-a][1,4]-benzodiazepin-1-one was reacted with the appropriate amine compound to obtain the following compounds.

| Ex. | |
|---|---|
| 9 | 8-chloro-1,2-dihydro-2-(morpholino) methylene-6-phenyl-1H,4H-imidazo-[1,2-a][1,4]-benzodiazepin-1-one. |
| 10 | 8-chloro-1,2-dihydro-2-(N-hydroxyethyl-piperazin-1-yl)methylene-6-phenyl-1H,4H-imidazo-[1,2-a][1,4]-benzodiazeoin-1-one. |
| 11 | 8-chloro-1,2-dihydro-2-(N-phenyl-piperazin-1-yl) methylene-6-phenyl-1H,4H-imidazo-[1,2-a][1,4]-benzodiazepin-1-one. |
| 12 and 12B | 8-chloro-1,2-dihydro-2-(N-methyl-piperazin-1-yl) methylene-6-(o-chlorophenyl)-1H,4H-imidazo-[1,2-a][1,4]-benzodiazepin-1-one and its tartrate. |
| 13 | 8-nitro-1,2-dihydro-2-(N-methyl-piperazin-1-yl) methylene-6-phenyl-1H,4H-imidazo-[1,2-a][1,4]-benzodiazepin-1-one. |
| 14 | 8-chloro-1,2-dihydro-2-(piperazin-1-yl) methylene-6-phenyl-1H,4H-imidazo-[1,2-a][1,4]-benzodiazepin-1-one. |
| 15 | 8-chloro-1,2-dihydro-2-(n-butyl-amino) methylene-6-phenyl-1H,4H-imidazo/1,2-a//1,4/-benzodiazepin-1-one. |
| 16 | 8-chloro-1,2-dihydro-2-(piperidino) methylene-6-phenyl-1H,4H-imidazo-[1,2-a][1,4]-benzodiazepin-1-one. |
| 17 | 8-chloro-1,2-dihydro-2-(thiomorpholino) methylene-6-phenyl-1H,4H-imidazo-[1,2-a][1,4]-benzodiazepin-1-one. |
| 18 | 8-chloro-1,2-dihydro-2-(diethylaminoethylamino) methylene-6-phenyl-1H,4H-imidazo-[1,2-a][1,4]-benzodiazepin-1-one. |
| 19 | 8-chloro-1,2-dihydro-2-(N-methyl-N-(dimethylamino) ethylamino) methylene-6-phenyl-1H,4H-imidazo-[1,2-a][1,4]-benzodiazepin-1-one. |
| 20 | 8-chloro-1,2-dihydro-2-(methylamino) methylene-6-phenyl-1H,4H-imidazo-[1,2-a][1,4]-benzodiazepin-1-one. |
| 21 | 8-chloro-1,2-dihydro-2-(cyclohexylamino) methylene-6-phenyl-1H,4H-imidazo-[1,2-a][1,4]-benzodiazepin-1-one. |
| 22 | 8-chloro-1,2-dihydro-2-(N-methyl-piperazin-1-yl) methylene-6-(o-fluorophenyl)-1H,4H-imidazo-[1,2-a][1,4]-benzodiazepin-1-one. |
| 23 | 8-chloro-1,2-dihydro-2-[ 4-(1'-phenyl-5'-imidazolyl-4'-one)piperidin-1-yl]methylene-6-phenyl-1H,4H-imidazo-[1,2-a][1,4]-benzodiazepin-1-one. |
| 24 | 8-chloro-1,2-dihydro-2-(phenylamino) methylene-6-phenyl-1H,4H-imidazo-[1,2-a][1,4]-benzodiazepin-1-one. |
| 25 | 8-chloro-1,2-dihydro-2-(t-butylamino) methylene-6-phenyl-1H,4H-imidazo-[1,2-a][1,4]-benzodiazepin-1-one. |
| 26 | 8-chloro-1,2-dihydro-2-(hydroxyethylamino) methylene-6-phenyl-1H,4H-imidazo-[1,2-a][1,4]-benzodiazepin-1-one. |
| 27 | 8-chloro-1,2-dihydro-2-(n-propylamino) methylene-6-phenyl-1H,4H-imidazo-[1,2-a][1,4]-benzodiazepin-1-one. |
| 28 | 8-nitro-1,2-dihydro-2-(N-methyl-piperazin-1-yl) methylene-6-(o-chlorophenyl)-1H,4H-imidazo-[1,2-a][1,4]-benzodiazepin-1-one. |
| 29 | 8-nitro-1,2-dihydro-2-(N-methyl-piperazin-1-yl) methylene-6-(o-fluorophenyl)-1H,4H-imidazo-[1,2-a][1,4]-benzodiazepin-1-one. |
| 30 and 30 B | 8-chloro-1,2-dihydro-2-(N-ethyl-piperazin-1-yl) methylene-6-phenyl-1H,4H-imidazo-[1,2-a][1,4]-benzodiazepin-1-one and its tartrate. |
| 31 | 8-chloro-1,2-dihydro-2-(N-propyl-piperazin-1-yl) methylene-6-phenyl-1H,4H-imidazo-[1,2-a][1,4]-benzodiazepin-1-one. |
| 32 | 8-chloro-1,2-dihydro-2[N-(n-butyl)-piperazin-1-yl] methylene-6-phenyl-1H,4H-imidazo-[1,2-a][1,4]-benzodiazepin-1-one. |
| 33 | 8-chloro-1,2-dihydro-2-(N-ethyl-piperazin-1-yl) methylene-5-(o-chlorophenyl)-1H,4H-imidazo-/1,2-al /1,4/-benzodiazepin-1-one. |
| 34 | 8-chloro-1,2-dihydro-2-(N-ethyl-piperazin-1-yl) methylene-6-(o-fluorophenyl)-1H,4H-imidazo-/1,2-a/ [1,4]-benzodiazepin-1-one. |
| 35 | 8-nitro-1,2-dihydro-2-(N-ethyl-piperazin-1-yl) methylene-6-(o-chlorophenyl)-1H,4H-imidazo-[1,2-a] [1,4]-benzodiazepin-1-one. |
| 36 | 8-nitro-1,2-dihydro-2-(N-ethyl-piperazin-1-yl) methylene-6-(o-fluorophenyl)-1H,4H-imidazo-[(1,2-a] [1,4]-benzodiazepin-1-one. |
| 37 | 8-chloro-1,2-dihydro-2-(ethylamino) methylene-6-phenyl-1H,4H-imidazo-[1,2-a][1,4]-benzodiazepin-1-one. |
| 38 | 8-chloro-1,2-dihydro-2-(N-propyl-piperazin-1-yl) methylene-6-o-chlorophenyl-1H,4H-imidazo-[1,2-a] [1,4]-benzodiazepin-1-one. |
| 39 | 8-chloro-1,2-dihydro-2-(ethylamino) methylene-6-o-chlorophenyl-1H,4H-imidazo-[1,2-a][1,4]-benzodiazepin-1-one. |
| 40 | 8-chloro-1,2-dihydro-2-(n-propylamino) methylene-6-o-chlorophenyl-1H,4H-imidazo-[1,2-a][1,4]-benzodiazepin-1-one. |

EXAMPLE 41

8-chloro-1,2-dihydro-2-(amino) methylene-6-phenyl-1H,4H-imidazo-[1,2-a][1,4]-benzodiazepin-1-one 2.1 g of 8-chloro-1,2-dihydro-2-(dimethylamino) methylene-6-phenyl-1H,4H-imidazo-[1,2-a][1,4]-benzodiazepin-1-one were suspended in 100 ml of anhydrous methanol and the suspension was stirred and cooled in a dry-ice acetone bath. Ammonia gas was bubbled through the mixture for 15 minutes and the suspension was then warmed to room temperature, stirred for a further two days, and the solvent was evaporated. The solid residue was crystallized from a methanol-ethyl acetate mixture to obtain 1.9 g (98% yield) of 8-chloro-1,2-dihydro-2-(amino) methylene-6-phenyl-1H,4H-imidazo-[1,2-a][1,4]-benzodiazepin-1-one melting at 265°–267° C.

EXAMPLE 42

8-chloro-1,2-dihydro-2-[1-(N-methyl-piperazino)-ethylidene]-6-phenyl-1H,4H-imidazo-[1,2-a][1,4]-benzodiazepin-1-one 2.3 g of 8-chloro-2-[1'-(dimethylamino)-ethylidene]-1,2-dihydro-6-phenyl-1H,4H-imidazo-[1,2-a][1,4]-benzodiazepin-1-one and 15 ml of N-methyl-piperazine were stirred at 120° C under a nitrogen atmosphere for 9 hours. The cooled solution was poured into water and sodium chloride was added to complete precipitation. The brown precipitate was filtered off and dissolved in CHCl₃. The solution was washed with water, dried over MgSO₄, and evaporated to dryness to obtain a dark red oil. The oil crystallized on triturating with ether-methanol, and was crystallized from ethyl acetate to obtain 1.0 g (38% yield) of 8-chloro-2[1'-(N-methyl-piperazin-1-yl)-ethylidene]-1,2-dihydro-6-phenyl-1H,4H-imidazo-[1,2-a][1,4]-benzodiazepin-1-one melting at 193°-195° C.

EXAMPLE 43

8-chloro-1,2-dihydro-2-[N-(isopropyl)-piperazin-1-yl] methylene-6-phenyl-1H,4H-imidazo-[1,2-a][1,4]-benzodiazepin-1-one 1.5 g of 8-chloro-1,2-dihydro-2-(piperazin-1-yl) methylene-6-1H,4H-imidazo-[1,2-a][1,4]-benzodiazepin-1-one, 2.5 g of isopropyl iodide and 3.0 g of sodium carbonate were stirred at 80° C in 25 ml of acetonitrile and 5 ml of methylene chloride for 18 hours. The cooled solution was poured into water and was extracted with chloroform. The extracts were washed with water, dried over MgSO₄, and evaporated to dryness to obtain a pale yellow solid. Crystallization of the solid from ethyl acetate gave 1.2 g (73% yield) of 8-chloro-1,2-dihydro-2-(N-isopropyl-piperazin-1-yl) methylene-6-phenyl-1H,4H-imidazo-[1,2-a][1,4]-benzodiazepin-1-one melting at 146°-148° C.

EXAMPLES 44 – 45

Using the procedure of Example 43, the following compounds were prepared:

44 8-chloro-1,2-dihydro-2-(N-allyl-piperazin-1-yl) methylene-6-phenyl-1H,4H-imidazo-[1,2-a][1,4]-benzodiazepin-1-one melting at 187–188° C.

45 8-chloro-1,2-dihydro-2-(N-cyclopropylmethyl-piperazin-1-yl) methylene-6-phenyl-1H,4H-imidazo-[1,2-a][1,4]-benzodiazepin-1-one melting at 202–204° C.

EXAMPLE 46

8-1,2-dihydro-2-(N-dimethylphosphinylmethyl-piperazin-1-yl) methylene-6-phenyl-1H,4H-imidazo-[1,2-a][1,4]-benzodiazepin-1-one A mixture of 2.5 g of 8-chloro-1,2-dihydro-2-(piperazin-1-yl) methylene-6-phenyl-1H,4H-imidazo-[1,2-a][1,4]-benzodiazepin-1-one, 1.5 g of chloromethyl-dimethylphosphine oxide and 5.0 g of sodium carbonate in 80 ml of toluene was stirred under reflux for 3 days. The cooled suspension was distributed between chloroform and water and the chloroform extract was separated, dried over MgSO₄, and evaporated to dryness to obtain a pale yellow oil which crystallized with methanol. The solid (unrequired by-product) was filtered off and the filrate was evaporated to give a pale orange oil. This oil was dissolved in chloroform and chromatographed on Kieselgel.

Elution with chloroform-methanol (5%) gave a pale yellow solid, which on crystallization from methylene chloride-ether gave 1.25 g (41% yield) of 8-chloro-1,2-dihydro-2-(N-dimethylphosphinylmethyl-piperazin-1-yl) methylene-6-phenyl-1H,4H-imidazo-[1,2-a][1,4]-benzodiazepin-1-one melting at 261°-262° C.

The analysis of IR spectra for the compounds of Examples 9 to 46 are reported in the following Table.

| | Formula Ib/1c | | | | | Analyses Found/Calculated | | | | Infrared Spectra cm⁻¹ (KBr Disc) | | | |
|---|---|---|---|---|---|---|---|---|---|---|---|---|---|
| Ex. | R | R₁ | —N(R₃)(R₄) | Molecular Formula | M.Wt. | %C | %H | %N | %Cl | NH, OH | C=O | C=N | melting point ° C |
| 9 | Cl | H | morpholino | $C_{22}H_{19}ClN_4O_2$ | 406.9 | 64.89 / 64.95 | 4.68 / 4.68 | 13.79 / 13.78 | 8.87 / 8.73 | — | 1695 | 1630 | 223.4 |
| 10 | Cl | H | N-hydroxyethyl-piperazin-1-yl | $C_{24}H_{24}ClN_5O_2$ | 450.0 | 63.91 / 64.07 | 5.41 / 5.34 | 15.59 / 15.57 | 8.15 / 7.90 | 3380 (OH) | 1690 | 1630 | 177.9 |
| 11 | Cl | H | N-phenylpiperazin-1-yl | $C_{28}H_{24}ClN_5O$ | 482.0 | 69.68 / 69.77 | 5.10 / 4.98 | 14.39 / 14.54 | 7.48 / 7.37 | — | 1695 | 1630 | 206.8 |
| 12 | Cl | Cl | N-methylpiperazin-1-yl | $C_{23}H_{21}Cl_2N_5O$ | 455.4 | 60.91 / 60.80 | 4.72 / 4.66 | 15.35 / 15.41 | 15.46 / 15.61 | — | 1695 | 1625 | 247.8 |
| 12B | Cl | Cl | N-methylpiperazin-1-yl | $C_{27}H_{27}Cl_2N_5O_7$ | 604.5 | — / 53.66 | — / 4.50 | — / 11.59 | — / 11.73 | — | — | — | 155–160 |
| 13 | NO₂ | H | N-methylpiperazin-1-yl | $C_{23}H_{22}N_6O_3$ | 430.5 | 63.80 / 64.18 | 5.17 / 5.12 | 19.54 / 19.54 | — / — | — | 1692 | 1635 | 284.6 |
| 14 | Cl | H | piperazin-1-yl | $C_{22}H_{20}ClN_5O$ | 405.9 | 65.05 / 65.10 | 5.03 / 4.93 | 17.25 / 17.26 | 9.09 / 8.75 | 3300 (NH) | 1695 | 1625 | 233.5 |
| 15 | Cl | H | N-butylamino | $C_{22}H_{21}ClN_4O$ | 392.9 | 66.96 / 67.25 | 5.46 / 5.35 | 14.13 / 14.27 | 9.24 / 9.04 | 3200 (NH) | 1690 | 1638 | 165.7 |
| 16 | Cl | H | piperidino | $C_{23}H_{21}ClN_4O$ | 404.9 | 68.08 / 68.24 | 5.29 / 5.23 | 14.13 / 13.84 | 8.77 / 8.73 | — | 1690 | 1625 | 249.50 |
| 17 | Cl | H | thiomorpholino | $C_{22}H_{19}ClN_4OS$ | 422.9 | 62.02 / 62.49 | 4.62 / 4.53 | 13.05 / 13.25 | — / 8.36 | — | 1700 | 1630 | 255.8 |
| 18 | Cl | H | diethylaminoethylamino | $C_{24}H_{26}ClN_5O$ | 436.0 | 66.38 / 66.13 | 6.28 / 5.97 | 16.26 / 16.07 | 8.04 / 8.15 | 3210 (NH) | 1690 / — | 1640 / 1630 | 113.6 |
| 19 | Cl | H | N-methyl-N-(dimethylamino)-ethylamino | $C_{23}H_{24}ClN_5O$ | 422.0 | 65.33 / 65.49 | 5.71 / 5.37 | 16.27 / 16.60 | 8.50 / 8.38 | — | 1690 | 1630 | 152.5 |
| 20 | Cl | H | methylamino | $C_{19}H_{15}ClN_4O$ | 350.9 | 64.86 / 65.07 | 4.46 / 4.31 | 15.74 / 15.98 | 10.20 / 10.08 | 3300 (NH) | 1690 | 1620 | 233.5 |
| 21 | Cl | H | cyclohexylamino | $C_{24}H_{23}ClN_4O$ | 419.0 | 68.35 / 68.82 | 5.78 / 5.49 | 13.53 / 13.39 | 8.18 / 8.48 | 3420 (NH) | 1695 | 1635 | 143.5 |
| 22 | Cl | F | N-methylpiperazin-1-yl | $C_{23}H_{21}ClFN_5O$ | 438.0 | 62.44 / 63.08 | 4.91 / 4.83 | 15.68 / 15.59 | 8.57 / 8.09 | — | 1700 | 1630 | 249.51 |
| 23 | Cl | H | 4-(1'-phenyl-5'-imidazoyl-4'-one)piperidin-1-yl | $C_{31}H_{27}ClN_6O_2$ | 551.1 | — / 67.57 | — / 4.94 | — / 15.25 | — / 6.43 | 3400 (NH) | 1715 / 1680 | 1620 | 289.91 |
| 24 | Cl | H | phenylamino | $C_{24}H_{17}ClN_4O$ | 412.9 | 69.61 / 68.82 | 4.19 / 4.15 | 13.40 / 13.57 | 8.97 / 8.59 | 3400 (NH) | 1690 / 1678 | 1650 | 249.51 |
| 25 | Cl | H | t-butylamino | $C_{22}H_{21}ClN_4O$ | 392.9 | — | — | — | — | 3320 | 1690 | 1640 | 230.2 |

-continued

| | Formula Ib/1c | | | Molecular Formula | M.Wt. | Analyses Found/Calculated | | | | Infrared Spectra cm⁻¹ (KBr Disc) | | | melting point °C |
|---|---|---|---|---|---|---|---|---|---|---|---|---|---|
| Ex. | R | $R_1$ | $-N(R_3)(R_4)$ | | | %C | %H | %N | %Cl | NH, OH | C=O | C=N | |
| 26 | Cl | H | hydroxyethyl amino | $C_{20}H_{17}ClN_4O_2$ | 380.9 | 67.26 / 62.98 | 5.39 / 4.72 | 14.26 / 14.65 | 9.02 / 9.58 | (NH) 3280 | 1700 | 1630 | 223.5 |
| 27 | Cl | H | n-propylamino | $C_{21}H_{19}ClN_4O$ | 378.9 | 63.08 / 66.48 | 4.50 / 5.09 | 14.71 / 14.64 | 9.31 / 9.43 | (NH) 3230 | 1700 | 1630 | 153.5 |
| 28 | $NO_2$ | Cl | N-methylpiperazin-1-yl | $C_{23}H_{21}ClN_6O_3$ | 465.0 | 66.58 / 59.31 / 59.43 | 5.02 / 4.68 / 4.55 | 14.79 / 18.00 / 18.08 | 9.38 / 7.85 / 7.63 | (NH) — | 1690 | 1630 | 214.5 |
| 29 | $NO_2$ | F | N-methylpiperazin-1-yl | $C_{23}H_{21}FN_6O_3$ | 448.5 | 61.43 / 61.60 | 4.83 / 4.72 | 18.82 / 18.74 | — / — | — | 1690 | 1630 | 303.6 |
| 30 | Cl | H | N-ethylpiperazin-1-yl | $C_{24}H_{24}ClN_5O$ | 434.0 | — / 66.43 | — / 5.57 | — / 16.14 | — / 8.17 | — | 1695 | 1630 | 183.4 |
| 30B | Cl | H | N-ethyl piperazin-1-yl | $C_{28}H_{30}ClN_5O_7$ | 584.1 | 56.55 / 57.57 | 5.16 / 5.13 | 11.44 / 11.99 | 6.15 / 6.08 | 3400 2500 | 1710 1690 | 1630 | 143.7 |
| 31 | Cl | H | N-propylpiperazin-1-yl | $C_{25}H_{26}ClN_5O$ | 448.0 | — / 67.03 | — / 5.85 | — / 15.63 | — / 7.91 | — | 1695 | 1630 | 148.52 |
| 32 | Cl | H | N-(n-butyl)-piperazin-1-yl | $C_{26}H_{28}ClN_5O$ | 462.0 | 67.46 / 67.61 | 6.16 / 6.07 | 15.10 / 15.17 | 7.73 / 7.69 | — | 1697 | 1630 | 186.7 |
| 33 | Cl | Cl | N-ethyl-piperazin-1-yl | $C_{24}H_{23}Cl_2N_5O$ | 469.4 | 61.75 / 61.54 | 5.11 / 4.95 | 14.35 / 14.95 | 15.03 / 15.14 | — | 1695 | 1632 | 243.5 |
| 34 | Cl | F | N-ethyl-piperazin-1-yl | $C_{24}H_{23}ClFN_5O$ | 452.0 | 63.04 / 63.19 | 5.17 / 5.13 | 15.19 / 15.50 | 7.96 / 7.84 | — | 1697 | 1637 | 235.7 |
| 35 | $NO_2$ | Cl | N-ethyl-piperazin-1-yl | $C_{24}H_{23}ClN_6O_3$ | 480.0 | 60.25 / 60.19 | 4.90 / 4.81 | 17.45 / 17.56 | 7.86 / 7.42 | — | 1697 | 1640 | 265.7 |
| 36 | $NO_2$ | F | N-ethyl-piperazin-1-yl | $C_{24}H_{23}FN_6O_3$ | 462.5 | 62.28 / 62.33 | 5.15 / 5.01 | 17.95 / 18.17 | — / — | — | 1693 | 1630 | 262.4 |
| 37 | Cl | H | Ethylamino | $C_{20}H_{17}ClN_4O$ | 364.8 | 65.36 / 65.85 | 4.72 / 4.66 | 15.03 / 15.37 | 9.56 / 9.74 | 3250 (NH) | 1690 | 1640 | 234.6 |
| 38 | Cl | Cl | N-(n-propyl)-piperazin-1-yl | $C_{25}H_{25}Cl_2N_5O$ | 483.5 | 62.31 / 62.24 | 5.28 / 5.22 | 14.67 / 14.52 | 14.67 / 14.70 | — | 1696 | 1632 | 247.9 |
| 39 | Cl | Cl | Ethylamino | $C_{20}H_{16}Cl_2N_4O$ | 399.3 | 60.21 / 60.16 | 4.05 / 4.04 | 13.90 / 14.03 | 17.95 / 17.76 | 3280 (NH) | 1700 | 1646 | 235.7 |
| 40 | Cl | Cl | n-propylamino | $C_{21}H_{18}Cl_2N_4O$ | 413.4 | 61.02 / 61.03 | 4.37 / 4.39 | 13.36 / 13.56 | 17.32 / 17.16 | 3240 (NH) | 1695 | 1640 | 227.9 |
| 41 | Cl | H | amino | $C_{18}H_{13}ClN_4O$ | 336.8 | 64.22 / 64.19 | 3.92 / 3.86 | 16.68 / 16.64 | 10.53 / 10.54 | 3320 3180 (NH) | 1690 1665 | 1640 1625 | 265.7 |
| 42 | Cl | H | N-methylpiperazino | $C_{24}H_{24}ClN_5O$ | 434.0 | 66.32 / 66.43 | 5.50 / 5.54 | 15.98 / 16.14 | 8.11 / 8.38 | — | 1660 | 1615 | 193.5 |
| 43 | Cl | H | N-(isopropyl)-piperazin-1-yl | $C_{25}H_{26}ClN_5O$ | 448.0 | 66.71 / 67.05 | 5.94 / 5.89 | 15.90 / 15.62 | 7.92 / 8.14 | — | 1698 | 1630 | 146.8 |
| 44 | Cl | H | N-allylpiperazin-1-yl | $C_{25}H_{24}ClN_5O$ | 446.0 | 67.02 / 67.33 | 5.41 / 5.39 | 15.62 / 15.71 | 8.00 / 7.97 | — | 1695 | 1635 | 187.8 |
| 45 | Cl | H | N-(cyclopropyl-methyl)-piperazin-1-yl | $C_{26}H_{26}ClN_5O$ | 460.0 | 67.87 / 67.90 | 5.73 / 5.66 | 15.18 / 15.24 | 7.80 / 7.73 | — | 1695 | 1630 | 202.4 |
| 46 | Cl | H | N-(dimethylphosphinyl-methyl)-piperazin-1-yl | $C_{25}H_{27}ClN_5PO_2$ | 496.1 | — / 60.54 | — / 5.45 | — / 7.16 | — / 14.13 | — | 1692 | 1630 | 261.2 |

EXAMPLE 47

8-chloro-1,2-dihydro-2-(N-dimethylphosphinyl-methyl-piperazin-1-yl) methylene-6-(o-chlorophenyl)-1H,4H-imidazo-[1,2-a][1,4]-benzodiazepin-1-one A mixture of 850 mg of 8-chloro-1,2-dihydro-2-(piperazin-1-yl) methylene-6-(o-chlorophenyl)-1H,4H-imidazo-[1,2-a][1,4]-benzodiazepin-1-one, 1.0 g of chloromethyl-dimethylphosphine oxide, 1.0 g of sodium iodide and 2.0 g of sodium carbonate in 50 ml of dry toluene was stirred under reflux for 24 hours. The cooled solution was partitioned between chloroform and water and the chloroform extract was separated, dried over magnesium sulfate and evaporated to dryness to obtain a gummy solid. The product was chromatographed over silica and was eluted with chloroform to give a solid which on crystallization from methanol-ethyl acetate-ether gave 8-chloro-1,2-dihydro-2-(N-dimethylphosphinylmethyl-piperazin-1-yl) methylene-6-(o-chlorophenyl)-1H,4H-imidazo-[1,2-a][1,4]-benzodiazepin-1-one with a melting point of 231°-234° C.
I.R. Spectra (KBr disc):
C=O at 1700 cm⁻¹; C=N at 1630 cm⁻¹.

EXAMPLE 48

1,2-dihydro-2-(N-dimethylphosphinylmethylpiperazin-1-yl) methylene-6-phenyl-1H,4H-imidazo-[1,2-a][1,4]-benzodiazepin-1-one Using the method of Example 47, 1,2-dihydro-2-(piperazin-1-yl) methylene-6-phenyl-1H,4H-imidazo-[1,2-a][1,4]-benzodiazepin-1-one was reacted to form 1,2-dihydro-2-(N-dimethylphosphinylmethylpiperazin-1-yl) methylene-6-phenyl-1H,4H-imidazo-[1,2-a][1,4]-benzodiazepin-1-one melting at 245°-247° C.
I.R. Spectra (KBr disc):
C=O at 1695 cm⁻¹; C=N at 1630 cm⁻¹.

EXAMPLE 49

8-nitro-1,2-dihydro-2-(N-dimethylphosphinylmethyl-piperazin-1-yl) methylene-6-(o-chlorophenyl)-1H,4H-imidazo-[1,2-a][1,4]-benzodiazepin-1-one Using the method of Example 47, 8-nitro-1,2-dihydro-2-(piperazin-1-yl) methylene-6-(o-chlorophenyl)-1H,4l-imidazo-1,2-a][1,4]-benzodiazepin-1-one was reacted to form 8-nitro-1,2-dihydro-2-(N-dimethylphosphinylmethyl-piperazin-1-yl) methylene-6-(o-chlorophenyl)-

1H,4H-imidazo-[1,2-a][1,4]-benzodiazepin-1-one melting at 245°–248° C.
I.R. Spectra (KBr disc):
C=O at 1700 cm$^{-1}$; C=N at 1642 cm$^{-1}$

EXAMPLE 50

8-nitro-1,2-dihydro-2-(N-methyl-piperazin-1-yl) methylene-6-(o-chlorophenyl)-1H,4H-imidazo-[1,2-a][1,4]-benzodiazepin-1-one methanesulfonate 1.1 g of methansulfonic acid were added dropwise to a mixture of 4.6 g of 8-nitro-1,2-dihydro-2-(N-methyl-piperazin-1-yl) methylene-6-(o-chlorophenyl)-1H,4H-imidazo-[1,2-a][1,4]-benzodiazepin-1-one in 100 ml of anhydrous methylene chloride and 5 ml of methanol. Dry ether was slowly added until crystals formed on scratching and the solution was allowed to crystallize with further ether being added to complete the crystallization. The pale yellow solid was filtered off, washed with ether and crystallized from methylene chloride-methanol to obtain 5.4 g of 8-nitro-1,2-dihydro-2-(N-methyl-piperazin-1-yl) methylene-6-(o-chlorophenyl)-1H,4H-imidazo-[1,2-a][1,4]-benzodiazepin-1-one methanesulfonate melting at 205°–210° C.

EXAMPLE 51

Tablets were prepared having the following constituents per tablet:

5 mg of 8-chloro-1,2-dihydro-2-(N-methylpiperazin-1-yl) methylene-6-phenyl-1H,4H-imidazo[1,2-a][1,4]-benzodiazepin-1-one and sufficient excipient of lactose, starch, talc and magnesium stearate to obtain a tablet of 100 mg.

The ingredients for gelatin capsules were prepared having the following constituents per capsule:

5 mg of 8-chloro-1,2-dihydro-2-(N-methylpiperazin-1-yl) methylene-6-phenyl-1H,4H-imidazo-[1,2-a][1,4]-benzodiazepin-1-one tartrate and sufficient excipient of talc, starch and magnesium stearate for a gelatin capsule weighing 100 mg.

Injectable ampoules were prepared containing a solution having the following constituents: 10 mg of 8-chloro-1,2-dihydro-2-(N-methylpiperazin-1-yl) methylene-6-phenyl-1H,4H-imidazo-[1,2-a][1,4]-benzodiazepin-1-one tartrate and sufficient aqueous solvent to obtain a final volume of 2 ml.

Tablets were prepared having the following constituents per tablets:

5 mg of 8-chloro-1,2-dihydro-2-(N-methylpiperazin-1-yl) methylene-6-(o-chlorophenyl)-1H,4H-imidazo-[1,2-a][1,4]-benzodiazepin-1-one and enough excipient of lactose, starch, talc and magnesium stearate to obtain a tablet weighing 100 mg.

Tablets were prepared having the following constituents per tablets:

5 mg of 8-chloro-1,2-dihydro-2-(N-methylpiperazin-1-yl) methylene-6-(o-fluorophenyl)-1H,4H-imidazo[1,2-a][1,4]-benzodiazepin-1-one and sufficient excipient for a tablet weighing 100 mg of lactose, starch, talc and magnesium stearate.

Tablets were prepared having the following constituents per tablets:

5 mg of 8-nitro-1,2-dihydro-2-(N-methylpiperazin-1-yl) methylene-6-(o-chlorophenyl)-1H,4H-imidazo[1,2-a][1,4]-benzodiazepin-1-one and sufficient excipient for a tablet weighing 100 mg of lactose, starch, talc and magnesium stearate.

Tablets were prepared having the following constituents per tablets:

5 mg of 8-nitro-1,2-dihydro-2-(N-methyl-piperazin-1-yl) methylene-6-(o-chlorophenyl)-1H,4H-imidazo-[1,2-a][1,4]-benzodiazepin-1-one methanesulfonate and sufficient excipient for a tablet weighing 100 mg of lactose, starch, talc and magnesium stearate.

Tablets were prepared having the following constituents per tablets:

5 mg of 8-chloro-1,2-dihydro-1-(N-methyl-piperazin-1-yl) methylene-6-(o-chlorophenyl)-1H,4H-imidazo-[1,2-a][1,4]-benzodiazepin-1-one tartrate and sufficient excipient for a tablet weighing 100 mg of lactose, starch, talc and magnesium stearate.

PHARMACOLOGICAL ACTIVITY

1. Antiaggressive activity in mice (AAM)

Groups of 20 randomly selected male mice weighing 25–30 g (Tuck T.O. strain) were given oral doses of either the vehicle alone (10 ml per kg distilled water) or the vehicle plus the test compound. 30 minutes after dosing, pairs of mice were placed under an inverted 1 liter pyrex beaker on a metal grid. The grid was connected to a Palmer square wave stimulator, and the feet of the mice were electrically stimulate with 90 volt pulses of 5 milli-second duration at a frequency of 2 pulses per second for a period of 2 minutes. This procedure provoked fighting in the control mice with a fight being defined as a frontal aggressive attack, usually biting, by either mouse on the other one. The total number of fights in the control group was calculated.

The ED$_{50}$ of a test compound was that dose which caused a 50% reduction in the number of fights of the batch of mice given that compound as compared with the control batch. [Tedeschi. R. E. et al (1959) J. Pharm. Exptl. Ther. 125.28–34]

The results are shown in the Table below.

2. Anticonvulsant test against maximal electroshock in mice (AEM)

Groups of ten mice were injected orally with the test compound in a vehicle at various dose levels with a control group receiving the vehicle alone. 30 minutes after dosing, each group was then shocked via auricalar electrodes using electroshock apparatus (Ugo Basile ECT apparatus for small mammals). The shocks had a pulse width of 0.2 milliseconds, and a frequency of 100 Hz, and each shock was given for 0.2 seconds at a current of 55 milliamps. The number of mice which underwent tonic extension of their hind limbs was noted. The dose protecting 50% of the mice (TED$_{50}$), as compared with the control group, was noted, and the results are shown in the Table below.

3. Anticonvulsant test against pentylenetetrazole in mice (AIM)

Groups of ten mice were injected orally with the test compound in a vehicle at various dose levels with a control group receiving the vehicle alone. 30 minutes after dosing, each mouse received a sub-cutaneous injection of 130 mg/kg of pentylenetetrazole challenge (pentylenetetrazole is a central nervous system stimulant), and the mice were then individually housed in observation boxes. The number of mice showing tonic convulsions within 30 minutes of the pentylenetetrazole challenge was noted, and the results for the tonic phase were expressed as a percentage reduction of the control levels. From a constructed dose response curve, the doses protecting 50% of the mice (TED$_{50}$) against tonus were estimated, and are shown in Table 3 below.

4. Anticonvulsant test against strychnine in mice (ASM)

Groups of ten mice received the test compound and vehicle orally at various dose levels with a control group receiving the vehicle alone. 30 minutes after dosing, each mouse received a sub-cutaneous injection of 1 mg/kg of strychnine challenge (strychnine is a central nervous system stimulant), and the mice were then housed individually in observation boxes. The number of mice exhibiting tonic convulsions within 15 minutes of the strychnine challenge was noted, and the results for the tonic phase expressed as a percentage reduction of the control value. From a constructed dose response line, the doses protecting 50% of the mice (TED$_{50}$) against tonus were estimated, and are shown in Table 3 below.

5. Potentiation of hexobarbital in mice (PHM)

A group of ten control mice received an ED$_{20}$ dose of hexobarbital intraperitoneally (150 mg/kg) of hexobarbital which is a sedative and hypnotic, followed by an oral dose of either a vehicle alone or various oral doses of the vehicle and a test compound. The number of mice which exhibited loss of the righting reflex for 30 seconds half-an-hour after dosing was noted, and a dose response curve was constructed. The dose of test compound which causes 50% of the mice in a group to lose the righting reflex was estimated (ED$_{50}$), and the results are shown in Table 3 below.

6. Potentiation of chlorprothixene in mice (PXM)

Groups of 10 randomly selected male CFLP mice (Carworth Europe) weighing 20-25 g each were given chlorprothixene intraperitoneally (12.5 mg/kg of chlorprothixene which is a tranquillizer and antipsychotic). This dose consistently caused 10% of mice to lose their righting reflex 30 minutes after dosing. At the same time, the test groups of mice were given orally either vehicle alone (distilled water, 10 ml/kg), or a dose of vehicle plus test compound. Each mouse was then placed individually in a small observation chamber and tested for loss of righting reflex 30 minutes after dosing. The ED$_{50}$ value of a test compound was the dose which caused loss of the righting reflex in 50% of the number of mice in a group which, in the absence of oral treatment, would not be expected to lose their righting reflex. The results are shown in Table 3 below.

7. Rotating drum test in mice (RDM)

Groups of ten mice were injected orally with vehicle plus the test compound at various dose levels, with a control group receiving the vehicle alone. 30 minutes after dosing, each group of mice was placed on a 30 cm diameter rotating drum revolving at 1 revolution/minute. The mice were placed on the drum against its direction of movement, and the number of mice falling off within a 2 minutes test period was noted. From the results obtained, a dose response line was constructed, and the dose causing 50% of the mice to fall off the drum (ED$_{50}$) was estimated. The results are shown in Table 3 below.

8. Mouse Acute Toxicity Test (ATM)

Acute toxicity test by oral and intraperitoneal routes were conducted using groups of ten mice at various dose levels. The groups were assessed for mortality at 24 hours, and the results are shown in Table 3 below given in mg/kg.

| The compound of Example | AAM (anti-aggression) | AMM (electro-shock) | ALM (pentylene-tetrazole) | ASH (strychnine) | PHM (hexo-barbital) | PXM (chlorpro-thixene) | RDM (drum) | ATM ip (toxicity) | ATM po (toxicity) |
|---|---|---|---|---|---|---|---|---|---|
| 8A | 2.65 | 4.1 | 0.8 | 7.1 | 4.9 | 5.4 | 7.1 | >1000 | >1000 |
| 8B | 4 | 4.2 | 0.8 | 7.4 | 2.55 | 6.8 | 1.7 | — | — |
| 10 | 4 | 12.5 | 1.85 | ∫50 | 14 | 29 | — | >1000 | >1000 |
| 12 | 0.2 | 2.1 | 0.165 | 1.8 | 0.038 | 1.6 | 0.78 | >1000 | >1000 |
| 12B | — | — | — | — | — | 2.67 | — | — | — |
| 13 | 2.2 | 4.2 | 0.92 | 6.6 | 3.6 | 4.5 | 8.6 | >1000 | >1000 |
| 15 | 3.35 | 12.5 | 1.15 | 17 | 0.66 | 1.8 | 24 | >1000 | >1000 |
| 21 | 1.4 | 8.5 | 2.35 | 15 | 8.3 | 6.2 | — | — | — |
| 22 | 0.34 | 0.27 | 0.115 | 1.3 | 0.21 | 1.35 | 2.6 | >1000 | >1000 |
| 27 | 0.92 | 4.0 | >1, <2 | 50 | 3.9 | 2.6 | 2.85 | — | — |
| 28 | 0.42 | 0.76 | 0.028 | 0.41 | 1.0 | 1.1 | 2.2 | — | — |
| 29 | 0.26 | 1.2 | 0.13 | 0.46 | 0.8 | 1.6 | 1.5 | — | — |
| 30 | 0.94 | 2.2 | 0.48 | 5.5 | 1.1 | 5.0 | 1.6 | — | — |
| 30B | 0.62 | 8.3 | 1.45 | 30 | >50 | 9.5 | 7.4 | — | — |
| 31 | 1.3 | 2.7 | >1, <2 | 6.4 | 3.6 | 3.2 | 1.1 | — | — |
| 33 | 0.5 | 2.2 | 0.087 | 2.3 | 2.5 | 1.2 | 0.56 | — | — |
| 34 | 0.48 | 1.55 | — | 1.6 | 2.8 | 2.35 | 0.7 | — | — |
| 35 | 0.03 | — | 0.15 | — | — | 0.99 | — | — | — |
| 36 | 0.64 | — | — | — | 0.8 | — | — | — | — |
| 37 | 1.45 | — | — | — | 0.72 | — | — | — | — |
| 38 | 0.66 | 3.5 | 0.185 | 1.85 | 0.064 | 1.7 | 0.29 | — | — |
| 39 | 1.0 | 18.0 | 0.39 | 25 | 0.27 | 9.6 | 11.5 | — | — |
| 40 | 2.4 | >30 | 1.0 | >25 | 0.06 | 5.6 | 8.0 | — | — |
| 46 | 0.84 | — | — | — | — | — | — | — | — |
| 50 | 0.42 | 0.76 | 0.03 | 0.41 | 1.0 | 1.1 | 0.85 | — | — |

The results obtained show that the compounds of the invention possess a very important activity on the central nervous sytem as anticonvulsant, anti-anxiety and hypnotic sedatives, and that they have a very low toxicity.

Various modifications of the products and method of the invention may be made without departing from the spirit or scope thereof and it should be understood that the invention is to be limited only as defined in the appended claims.

I claim:

1. A compound selected from the group consisting of 1,2-dihydro-6-phenyl-1H,4H-imidazo-benzodiazepin-1-ones of the formula

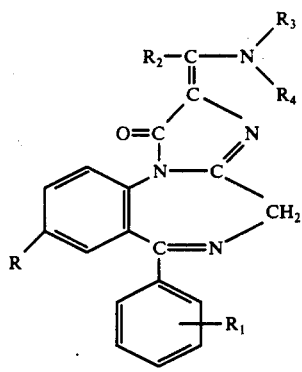

wherein R is selected from the group consisting of hydrogen, halogen, nitro and trifluoromethyl, $R_1$ is selected from the group consisting of hydrogen and halogen, $R_2$ is selected from the group consisting of hydrogen and methyl and $R_3$ and $R_4$ taken together with the nitrogen atom to which they are attached from a piperazinyl optionally substituted with at least one member of the group consisting of alkyl of 1 to 5 carbon atoms, hydroxyalkyl of 1 to 5 carbon atoms, hydroxyalkyl of 1 to 5 carbon atoms, dialkylphosphinylalkyl with 1 to 5 carbon atoms in the alkyl groups, cycloalkylalkyl with 3 to 6 carbon atoms in the ring and 1 to 5 alkyl carbon atoms, alkenyl of 2 to 5 carbon atoms and phenyl and their non-toxic, pharmaceutically acceptable acid addition salts.

2. A compound of claim 1 wherein $R_3$ and $R_4$ together with the nitrogen atom form a member selected from the group consisting of piperazin-1-yl, 4-alkyl-piperazin-1-yl, 4-hydroxyalkyl-piperazin-1yl and 4-phenyl-piperazin-1-yl.

3. A compound of claim 1 wherein R is selected from the group consisting of chlorine and nitro, $R_1$ is selected from the group consisting of hydrogen, chlorine and fluorine, $R_2$ is hydrogen and $R_3$ and $R_4$ together with the nitrogen atom form a member selected from the group consisting of piperazin-1-yl, 4-alkyl-piperazin-1-yl and 4-hydroxyethyl-piperazin-1-yl.

4. A compound of claim 1 wherein R is selected from the group consisting of chlorine and nitro, $R_1$ is selected from the group consisting of hydrogen, chlorine and fluorine, $R_2$ is hydrogen and $R_3$ and $R_4$ together with the nitrogen atom form a member of the group consisting of piperazin-1-yl, 4-methyl-piperazin-1-yl, 4-ethyl-piperazin-1-yl, 4-propyl-piperazin -1-yl and 4-hydroxyethyl-piperazin-1-yl.

5. A compound of claim 1 wherein R is chlorine or nitro, $R_1$ is selected from the group consisting of hydrogen, chlorine and fluorine, $R_2$ is hydrogen and $R_3$ and $R_4$ together with the nitrogen atom form a member of the group consisting of 4-methyl-piperazin-1-yl, 4-ethyl-piperazin-1-yl and 4propyl-piperazin-1-yl.

6. A compound of claim 1 wherein R is selected from the group consisting of hydrogen, chlorine and nitro, $R_1$ is selected from the group consisting of hydrogen, chlorine and fluorine, $R_2$ is hydrogen and $R_3$ and $R_4$ together with the nitrogen atom form a 4-dialkylphosphinylalkyl-piperazin-1-yl.

7. A compound of claim 1 wherein R is selected from the group consisting of hydrogen, chlorine and nitro, $R_1$ is selected from the group consisting of hydrogen and chlorine, $R_2$ is hydrogen and $R_3$ and $R_4$ together with the nitrogen atom form a 4-dimethylphosphinylmethyl-piperazin-1-yl.

8. A compound of claim 1 in the form of an acid addition salt with an acid selected from the group consisting of hydrochloric acid, hydrobromic acid, hydroiodic acid, nitric acid, sulfuric acid, phosphoric acid, acetic acid, formic acid, benzoic acid, maleic acid, fumaric acid, succinic acid, tartaric acid, citric acid, oxalic acid, glyoxylic acid, aspartic acid, an alkanesulfonic acid and an arylsulfonic acid.

9. A compound of claim 1 selected from the group consisting of 8-chloro-1,2-dihydro-2-(N-methyl-piperazin-1-yl) methylene-6-phenyl-1H,4H-imidazo-[1,2-a][1,4]-benzodiazepin-1-one and its non-toxic, pharmaceutically acceptable acid addition salts.

10. A compound of claim 1 which is the 8-chloro-1,2-dihydro-2-(N-methyl-piperazin-1-yl) methylene-6-phenyl-1H, 4H-imidazo-/1,2-a//1,4/-benzodiazepin-1-one tartrate.

11. A compound of claim 1 selected from the group consisting of 8-chloro-1,2-dihydro-2-(N-methyl-piperazin-1-yl) methylene-6-(o-chlorophenyl)-1H,4H-imidazo-[1,2-a][1,4]-benzodiazepin-1-one and its non-toxic, pharmaceutically acceptable acid addition salts.

12. A compound of claim 1 selected from the goup consisting of 8-chloro-1,2-dihydro-2-(N-methyl-piperazin-1-yl) methylene-6-(o-fluorophenyl)-1H,4H-imidazo-[1,2-a][1,4]-benzodiazepin-1-one and its non-toxic, pharmaceutically acceptable acid addition salts.

13. A compound of claim 1 selected from the group consisting of -nitro-1,2-dihydro-2-(N-methyl-piperazin-1-yl) methylene-6-(o-chlorophenyl)-1H,4H-imidazo-[1,2-a][1,4-]-benzodiazepin-1-one and its non-toxic, pharmaceutically acceptable acid addition salts.

14. A compound of claim 1 selected from the group consisting of 8-nitro-1,2-dihydro-2-(N-methyl-piperazin-1-yl) methylene-6-(o-fluorophenyl)-1H,4H-imidazo-[1,2a][1,4]-benzodiazepin-1-one and its non-toxic, pharmaceutically acceptable acid addition salts.

15. A compound of claim 1 selected from the group consisting of 8-chloro-1,2-dihydro-2-(N-dimethylphosphinylmethyl-piperazin-1-yl) methylene-6-phenyl-1H,4H-imidazo-[1,2-a][1,4]-benzodiazepin-1-one and its non-toxic, pharmaceutically acceptable acid addition salts.

16. The compound of claim 13 which is 8-nitro-1,2-dihydro-2-(N-methyl-piperazin-1-yl) methylene-6-(o-chlorophenyl)-1H,4H-imidazo-[1,2-a][1,4]-benzodiazepin-1one methanesulfonate.

17. A composition for the treatment of agitated states, insomnia and psychomatic syndromes comprising an effective amount of at least one compound of claim 1 and a pharmaceutical carrier.

18. A method for the treatment of states of agitation, insomnia and certain psychosomatic syndromes in warm-blooded animals comprising administering to warm-blooded animals an effective amount of at least one compund of claim 1.

19. The method of claim 18 wherein the compound is selected from the group consisting of 8-nitro-1,2-dihydro-2-(N-methylpiperazin-1-yl) methylene-6-(o-chlorophenyl)-1H,4Himidazo-[1,2-a][1,4]-benzodiazepin-1-one and its non-toxic, pharmaceutically acceptable acid addition salts.

20. The method of claim 18 wherein the compound is selected from the group consisting of 8-chloro-1,2-dihydro-2-(N-dimethylphosphinylmethyl)-piperazin-1-yl) methylene-6-phenyl-1H,4H-imidazo-[1,2-a][1,4-benzodiazepin-1-one and its nontoxic, pharmaceutically acceptable acid addition salts.

21. The method of claim 19 wherein the compound is in the form of its methanesulfonate salt.

* * * * *

UNITED STATES PATENT OFFICE
CERTIFICATE OF CORRECTION

Patent No. 4,044,142          Dated Aug. 23, 1977

Inventor(s) JOHN BODENHAM TAYLOR and DEREK RALPH HARRISON

It is certified that error appears in the above-identified patent and that said Letters Patent are hereby corrected as shown below:

| Col. | Line Claim 1 | Page | Line Claim 1 | |
|---|---|---|---|---|
| 21 | 22 | 47 | 15 | "from " should be --form-- |
| 22 | Claim 13 27 | 51 | 2 | "nitro" should be --8-nitro-- |

Signed and Sealed this

Sixth Day of June 1978

[SEAL]

Attest:

RUTH C. MASON
*Attesting Officer*

DONALD W. BANNER
*Commissioner of Patents and Trademarks*